United States Patent [19]
Geddes et al.

[11] Patent Number: 5,616,560
[45] Date of Patent: Apr. 1, 1997

[54] METHODS FOR THE TREATMENT OF OSTEOPOROSIS USING BISPHOSPHONATES AND PARATHYROID HORMONE

[75] Inventors: Ann D. Geddes, Norwich, N.Y.; Rogely W. Boyce, Pottstown, Pa.

[73] Assignee: The Procter & Gamble Company, Cincinnati, Ohio

[21] Appl. No.: 619,103

[22] Filed: Mar. 20, 1996

Related U.S. Application Data

[63] Continuation of Ser. No. 424,822, Apr. 19, 1995, abandoned, which is a continuation of Ser. No. 235,201, Apr. 29, 1994, abandoned, which is a continuation of Ser. No. 809,620, Dec. 17, 1991, abandoned.

[51] Int. Cl.$^6$ .................. C07K 1/00; A61K 38/27; A61K 38/00
[52] U.S. Cl. ........................................ 514/12; 514/21
[58] Field of Search ................................. 514/12, 21

[56] References Cited

U.S. PATENT DOCUMENTS

| | | | |
|---|---|---|---|
| 4,086,196 | 4/1978 | Tregear | 530/324 |
| 4,698,328 | 10/1987 | Neer et al. | 514/12 |
| 4,812,304 | 3/1989 | Anderson et al. | 424/112 |
| 4,822,609 | 4/1989 | Flora | 424/112 |
| 4,833,125 | 5/1989 | Neer | 514/12 |

FOREIGN PATENT DOCUMENTS

| | | |
|---|---|---|
| 3243358 | 5/1984 | Germany . |

OTHER PUBLICATIONS

Hesch, R. D. et al., "Results of a Stimulatory Therapy of Low Bone Metabolism in Osteoporosis with (1–38) hPTH and Diphosphonate EHDP–Protocol of Study I, Osteoporosis Trial Hannover" 66(19) *Klin Wschr.* 976–984 (Oct. 1988).

Delling, G., et al., "Morphologic Study of Pelvic Crest Spongiosa in Patients with Osteoporosis During ADFR Therapy with Parathyroid Hormone and Diphosphonates", 128(1) *Z. Orthop.* 1–5 (1990).

Delmas, et al., "The In Vivo Anabolic Effect of hPTH–(1–34) is Blunted When Bone Resorption Is Blocked By a Bisphosphonate", 6 (Supp. 1) *J. Bone Mineral Res.* §136 (Abst. 214) (Aug. 1991).

Hock, et al., "Resorption Is Not Essential for the Stimulation of Bone Growth by hPTH–(1–34) In Rats In Vivo", 4(3) *J. Bone Mineral Res* 449–458 (1989).

*Primary Examiner*—Howard S. Schain
*Assistant Examiner*—P. Lynn Touzeau
*Attorney, Agent, or Firm*—M. P. McMahon; K. F. Clark; J. C. Rasser

[57] ABSTRACT

The present invention provides methods of increasing bone mass in a human or other animal subject afflicted with osteoporosis, comprising a thirty(30)-day treatment period, comprised of a parathyroid hormone administration regimen and a bisphosphonate administration regimen, wherein (a) said parathyroid hormone administration regimen comprises the administration to said subject of parathyroid hormone at one or more level of from about 4 IU/kg per day to about 15 IU/kg per day that said parathyroid hormone is administered, provided that said parathyroid hormone is administered at least one day every seven days of every said thirty(30)-day treatment periods; and wherein (b) said bisphosphonate administration regimen comprises the administration to said subject of a bisphosphonate at a level of from about 0.0005 mgP/kg to about 1.0 mgP/kg per day that said bisphosphonate is administered, provided that said bisphosphonate is administered at least 1 day of every said thirty(30)-day treatment period.

24 Claims, No Drawings

METHODS FOR THE TREATMENT OF OSTEOPOROSIS USING BISPHOSPHONATES AND PARATHYROID HORMONE

This is a continuation of application Ser. No. 08/424,822, filed on Apr. 19, 1995, now abandoned which is a continuation of application Ser. No. 08/235,201, filed on Apr. 29, 1994, now abandoned, which is a continuation of application Ser. No. 07/809,620, filed on Dec. 17, 1991, now abandoned.

BACKGROUND OF THE INVENTION

This invention relates to methods of increasing bone mass in humans and other animals, i.e., for the treatment of osteoporosis and related bone metabolic disorders. In particular, this invention relates to such methods of treatment by the administration of a bone-active phosphonate and parathyroid hormone.

The most common metabolic bone disorder is osteoporosis. Osteoporosis can be generally defined as the reduction in the quantity of bone, or the atrophy of skeletal tissue. In general, there are two types of osteoporosis: primary and secondary. "Secondary osteoporosis" is the result of an identifiable disease process or agent. However, approximately 90% of all osteoporosis cases is "primary osteoporosis". Such primary osteoporosis includes postmenopausal osteoporosis, age-associated osteoporosis (affecting a majority of individuals over the age of 70 to 80), and idiopathic osteoporosis affecting middle-aged and younger men and women.

For some osteoporotic individuals the loss of bone tissue is sufficiently great so as to cause mechanical failure of the bone structure. Bone fractures often occur, for example, in the hip and spine of women suffering from postmenopausal osteoporosis. Kyphosis (abnormally increased curvature of the thoracic spine) may also result.

The mechanism of bone loss in osteoporotics is believed to involve an imbalance in the process of "bone remodeling". Bone remodeling occurs throughout life, renewing the skeleton and maintaining the strength of bone. This remodeling involves the erosion and filling of discrete sites on the surface of bones, by an organized group of cells called "basic multicellular units" or "BMUs". BMUs primarily consist of "osteoclasts", "osteoblasts", and their cellular precursors. In the remodeling cycle, bone is resorbed at the site of an "activated" BMU by an osteoclast, forming a resorption cavity. This cavity is then filled with bone by osteoblasts.

Normally, in adults, the remodeling cycle results in a small deficit in bone, due to incomplete filling of the bone resorption cavity. Thus, even in healthy adults, age-related bone loss occurs. However, in osteoporotics, there is an increase in the number of BMUs that are activated. This increased activation accelerates bone remodeling, resulting in abnormally high bone loss.

Although its etiology is not fully understood, there are many risk factors thought to be associated with osteoporosis. These include low body weight, low calcium intake, physical inactivity, and estrogen deficiency.

Many compositions and methods are described in the medical literature for the "treatment" of osteoporosis. Many of these compositions and methods attempt to either slow the loss of bone or to produce a net gain in bone mass. See, for example, R. C. Haynes, Jr. et al., "Agents affecting Calcification", *The Pharmacological Basis of Therapeutics*, 7th Edition (A. G. Gilman, L. S. Goodman et al., Editors, 1985); G. D. Whedon et al., "An Analysis of Current Concepts and Research Interest in Osteoporosis", *Current Advances in Skeletogenesis* (A. Ornoy et al., Editors, 1985); and W. A. Peck, et al., *Physician's Resource Manual on Osteoporosis* (1987), published by the National Osteoporosis Foundation.

Among the treatments for osteoporosis suggested in the literature is the administration of bisphosphonates or other bone-active phosphonates. See, for example, Storm et al., "Effect of Intermittent Cyclical Etidronate Therapy on Bone Mineralization and Fracture Rate in Women with Post-Menopausal Osteoporosis", 322 *New England Journal of Medicine* 1265 (1990); and Watts et al., "Intermittent Cyclical Etidronate Treatment of Post-Menopausal Osteoporosis", 323 *New England Journal of Medicine* 73 (1990). Such treatments using a variety of bisphosphonates are described in U.S. Pat. No. 4,761,406, Flora et al., issued Aug. 2, 1988; U.S. Pat. No. 4,812,304, Anderson et al., issued Mar. 14, 1989; U.S. Pat. No. 4,812,311, Uchtman, issued Mar. 14, 1989; and U.S. Pat. No. 4,822,609, Flora, issued Apr. 18, 1989. The use of such phosphonates for the treatment of osteoporosis, and other disorders involving abnormal calcium and phosphate metabolism, is also described in U.S. Pat. No. 3,683,080, Francis, issued Aug. 8, 1972; U.S. Pat. No. 4,330,537, Francis, issued Oct. 28, 1980; U.S. Pat. No. 4,267,108, Blum et al., issued May 12, 1981; European Patent Publication 298,553, Ebetino, published Jan. 11, 1989; and Francis et al., "Chemical, Biochemical, and Medicinal Properties of the Diphosphonates", *The Role of Phosphonates in Living Systems*, Chapter 4 (1983).

Parathyroid hormone has also been suggested as a therapy for osteoporosis. Such treatments using parathyroid hormone are disclosed in the following references, Hefti, et al., "Increase of Whole-Body Calcium and Skeletal Mass in Normal and Osteoporotic Adult Rats Treated with Parathyroid Hormone", 62 *Clin. Sci.* 389–396 (1982), German Patent Publication DE 39 35 738, Forssman, published May 8, 1991, U.S. Pat. No. 4,698,328, Neer, et al., issued Oct. 6, 1987, and U.S. Pat. No. 4,833,125, Neer, et al., issued May 23, 1989.

The effects of administering a bisphosphonate and a parathyroid hormone was studied in rats. The study concluded that bone mass increased more in rats treated with a bisphosphonate and parathyroid hormone than in rats treated solely with parathyroid hormone. See Hock, et al., "Resorption Is Not Essential for the Stimulation of Bone Growth by hPTH-(1-34) in Rats In Vivo", 4(3) *Jnl. of Bone and Mineral Res.* 449–458 (1989).

Cyclic administration of parathyroid hormone and bone-active phosphonates has been suggested as a therapy for osteoporosis in humans. Such treatments using bisphosphonates and parathyroid hormone are disclosed in the following references, all hereby incorporated by reference herein, U.S. Pat. No. 4,822,609, Flora, issued Apr. 18, 1989; U.S. Pat. No. 4,812,304, Anderson, et al., issued Mar. 14, 1989; German Patent Publication DE 32 43 358, Hesch, published May 24, 1984 and; Hesch, et al., "Results of a Stimulating Therapy of Low Bone Metabolism in Osteoporosis with (1-38h PTH and Diphosphonate EHDP" 66(19) *Klin. Wschr.* 976–984 (October 1988).

Additionally, the short term use of parathyroid hormone and bone-active phosphonates has been described in the following references: German Patent Publication DE 32 43 358, Hesch, published May 24, 1984 (hereinaftter "DE 32 43

358"); Hesch, et al., "Results of a Stimulatory Therapy of Low Bone Metabolism in Osteoporosis with (1-38)hPTH and Diphosphonate EHDP" 66(19) *Klin. Wschr.* 976–984 (October 1988) (hereinafter "Hesch, et al."); Delling, et al., "Morphologic Study of Pelvic Crest Spongiosa in Patients with Osteoporosis during ADFR Therapy with Parathyroid Hormone and Diphosphonates", 128(1) *Z. Orthop.* 1–5 (1990) (hereinafter "Delling, et al"); and Delmas, et al., "The In Vivo Anabolic Effect of hPTH-(1-34) Is Blunted When Bone Resorption Is Blocked By A Bisphosphonate" 6(1) *J. Bone Mineral Res.* S136 (#214) (August 1991) (hereinafter "Delmas").

However, the methods described in DE 32 43 358, and Hesch, et al., and Delling, et al., while useful in activating bone metabolism, have not been shown to be effective in increasing bone mass. Delling, et al. is especially skeptical of the effectiveness of a parathyroid hormone/bisphosphonate therapy for increasing bone mass. Delling, et al. conclude that a significant change in bone structure was not observed and that the utility of such a therapy is questionable. Delmas, is also skeptical of the effectiveness of parathyroid hormone and bisphosphonate therapy since his data indicate that parathyroid hormone is effective in increasing bone formation by itself but when administered in conjunction with a bisphosphonate the combination is less effective than the control (i.e. no treatment) in increasing bone formation.

Applicant has found, surprisingly, that the administration of bone-active phosphonates and parathyroid hormone increases bone mass. Accordingly, the methods of this invention provide effective methods of preventing and treating osteoporosis, with reduced side effects compared to such methods known in the art.

SUMMARY OF THE INVENTION

The present invention provides methods of increasing bone mass in a human or other animal subject afflicted with osteoporosis, comprising one or more thirty(30)-day treatment periods, comprised of a parathyroid hormone administration regimen and a bisphosphonate administration regimen, wherein (a) said parathyroid hormone administration regimen comprises the administration to said subject of parathyroid hormone at a level of from about 4 IU/kg per day to about 15 IU/kg per day that said parathyroid hormone is administered, provided that said parathyroid hormone is administered at least one day every seven days of every said thirty(30)-day treatment period; and wherein (b) said bisphosphonate administration regimen comprises the administration to said subject of a bisphosphonate at a level of from about 0.0005 mgP/kg to about 1.0 mgP/kg per day that said bisphosphonate is administered, provided that said bisphosphonate is administered at least 1 day of every said thirty(30)-day treatment period.

DESCRIPTION OF THE INVENTION

The methods of the present invention comprise the administration of bone-active phosphonates and parathyroid hormone to a human or other animal subject. Specific compounds and compositions to be used in these processes must, accordingly, be pharmaceutically-acceptable. As used herein, such a "pharmaceutically-acceptable" component is one that is suitable for use with humans and/or animals without undue adverse side effects (such as toxicity, irritation, and allergic response) commensurate with a reasonable benefit/risk ratio. Further, as used herein, the term "safe and effective amount" refers to the quantity of a component which is sufficient to yield a desired therapeutic response without undue adverse side effects (such as toxicity, irritation, or allergic response) commensurate with a reasonable benefit/risk ratio when used in the manner of this invention. The specific "safe and effective amount" will, obviously, vary with such factors as the particular condition being treated, the physical condition of the patient, the duration of the treatment, the nature of concurrent therapy (if any), and the specific formulations employed.

ACTIVE MATERIALS

Bone-Active Phosphonates:

The methods of this invention involve the administration of a bone-active phosphonate. As referred to herein, a "bone-active phosphonate" includes one or more compounds of the general formula

and pharmaceutically-acceptable salts and esters thereof, wherein A, B, and R are as defined hereinafter.

In Formula (1), "R" is hydroxy (for bisphosphonates), or hydrogen or alkyl (for phosphonoalkylphosphinates). In the phosphonoalkylphosphinates, R is preferably unsubstituted alkyl, especially lower alkyl. When R is substituted alkyl, preferred substituents include halogen, unsubstituted or substituted phenyl, unsubstituted or substituted pyridinyl, unsubstituted amino, amino substituted with one or two lower alkyl groups, hydroxy, or carboxy. More preferred substituents are fluoro, phenyl, unsubstituted amino, and hydroxy; most preferred are fluoro (especially when present as trifluoromethyl) and phenyl.

Particularly preferred R moieties in the phosphonoalkylphosphinates are unsubstituted lower alkyl groups, especially unsubstituted, straight-chain, saturated lower alkyl groups. Also preferred R moieties are methyl, ethyl, n-propyl, isopropyl, n-butyl, iso-butyl, sec-butyl, tert-butyl, and n-hexyl. More preferably, R is methyl, ethyl, n-propyl, or n-butyl. Most preferably, R is methyl.

In Formula (1), "A" is hydrogen; halogen; nitro; alkyl; heterocycle; aryl; heteroaryl; unsubstituted amino, or the amide thereof derived from a carboxylic acid of a substituent group; amino substituted with one substituent group, or the amide thereof derived from a carboxylic acid of a substituent group; amino substituted independently with one alkyl group and one substituent group; hydroxy, or the ester thereof derived from a carboxylic acid of a substituent group; ether having a substituent group; thiol, or the thiol ester thereof derived from a carboxylic acid of a substituent group; thioether having a substituent group, or the sulfoxide and sulfone derivative thereof; —SO$_3$H, the pharmaceutically-acceptable salts thereof, the ester thereof derived from an alcohol of a substituent group, the unsubstituted amide thereof, or the amide thereof substituted with one or two alkyl groups; —CO$_2$H, the pharmaceutically-acceptable salts thereof, the ester thereof derived from an alcohol of a substituent group, the unsubstituted amide thereof, or the amide thereof substituted with one or two alkyl groups; aldehyde; ketone having a substituent group; carbamate, unsubstituted or substituted with one or two alkyl groups; peptides having from about 1 to about 100 amino acid moieties; or the A and B moieties are covalently linked to form a ring having from 3 to 7 atoms with from 0 to 3 heteroatoms selected from the group consisting of nitrogen, sulfur, phosphorus and oxygen, the ring being unsubstituted or substituted with one or more of the above substituents of A; or the A and B moieties are replaced by an unsubstituted or substituted alkyl moiety attached to the geminal carbon (the carbon shown in structure (1) hereinabove) by a double bond.

Preferably, A is one of the following moieties.

(1) hydrogen (2) halogen (preferably fluoro or chloro, more preferably fluoro)

(3) substituted or unsubstituted alkyl having the general structure

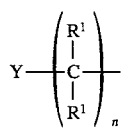  (2)

wherein:
 (a) n is an integer from 1 to 10, preferably from 1 to 5, more preferably 1 or 2, more preferably 1;
 (b) each $R^1$ is, independently, hydrogen, halogen, lower alkyl, unsubstituted amino or the amide thereof derived from a carboxylic acid of a lower alkyl group, amino substituted with one lower alkyl group or the amide thereof derived from a carboxylic acid of a lower alkyl group, amino substituted independently with two lower alkyl groups, hydroxy or the ester thereof derived from a carboxylic acid of a lower alkyl group, —$CO_2H$ or the pharmaceutically-acceptable salts thereof or the ester thereof derived from an alcohol of a lower alkyl group or the unsubstituted amide thereof or the amide thereof substituted with one or two lower alkyl groups, ether having a lower alkyl group, —$PO_3H_2$ or the pharmaceutically-acceptable salts thereof, and nitro, or two $R^1$'s on the same carbon atom are =O or =$NR^9$ (where $R^9$ is lower alkyl or may be hydrogen when there is another nitrogen atom attached to the same carbon atom as the =$NR^9$ moiety), or two $R^1$'s on adjacent carbon atoms may be replaced by an additional bond between the carbon atoms; or an $R^1$ on the first carbon atom (from the right side of structure (2) hereinabove) and B (see structure (1) hereinabove) may be replaced by an additional bond; and
 (c) Y is halogen; nitro; cyano; heterocycle; aryl; heteroaryl; unsubstituted amino, and the amide thereof derived from a carboxylic acid of an alkyl, heterocycle, aryl or heteroaryl group; amino substituted with one alkyl, heterocycle, aryl or heteroaryl group and the amide thereof derived from a carboxylic acid of an alkyl group; amino substituted independently with one alkyl group and one alkyl, heterocycle, aryl or heteroaryl group; hydroxy, and the ester thereof derived from a carboxylic acid of an alkyl, heterocycle, aryl or heteroaryl group; ether having an alkyl, heterocycle, aryl or heteroaryl group; thiol, and the thiol ester thereof derived from a carboxylic acid of an alkyl, heterocycle, aryl or heteroaryl group; thio-ether having an alkyl, heterocycle, aryl or heteroaryl group, and the sulfoxide and sulfone derivatives thereof; —$SO_3H$, the pharmaceutically-acceptable salts thereof, the ester thereof derived from an alcohol of an alkyl group, the unsubstituted amide thereof, and the amide thereof substituted with one or two alkyl groups; —$CO_2H$, the pharmaceutically-acceptable salts thereof, the ester thereof derived from an alcohol of an alkyl group, the unsubstituted amide thereof, and the amide thereof substituted with one or two alkyl groups; $PO_3H_2$, the pharmaceutically-acceptable salts thereof, the ester thereof derived from an alcohol of an alkyl group, the unsubstituted amide thereof, and the amide thereof substituted with one or two alkyl groups; —($R^8$)$PO_2H$ (where $R^8$ is hydrogen or unsubstituted lower alkyl), the pharmaceutically-acceptable salts thereof, the ester thereof derived from an alcohol of an alkyl group, the unsubstituted amide thereof, and the amide thereof substituted with one or two alkyl groups; aldehyde; ketone having an alkyl group; carbamate, unsubstituted or substituted with one or two alkyl groups; or peptidyl. For bisphosphonates, Y is preferably a heterocycle (preferably 5 to 7 membered heterocycles having one or two nitrogen atoms); amino; and substituted amino. Particularly preferred Y moieties include pyridyl, amino, and amino substituted with one or two lower alkyl groups. Preferably, for phosphonoalkylphosphinates, Y is halogen (preferably fluoro); trifluoromethyl; ether having a lower alkyl group; unsubstituted amino, and the amide thereof derived from a carboxylic acid of a lower alkyl group, amino substituted with one lower alkyl group and the amide thereof derived from carboxylic acid of a lower alkyl group; amino substituted independently with two lower alkyl groups; or peptidyl having from one to about six amino acid moieties.

(4) cycloalkyl having from 4 to 10 carbon atoms, preferably 5 or 6 carbon atoms (5) heterocycle having 5 or 6 atoms in the ring; more preferably one or two nitrogen atoms in the ring, more preferably having one nitrogen atom in the ring. Particularly preferred heterocycles are unsubstituted or substituted piperidinyl, pyrrolidinyl, piperazinyl, and morpholinyl.

(6) unsubstituted and substituted phenyl and naphthyl (7) unsubstituted and substituted 5 and 6 membered ring heteroaryls having one or two heteroatoms (especially nitrogen heteroatoms), preferably pyridinyl (8) an amine-containing moiety having the general structure:

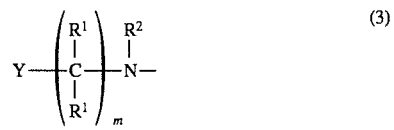  (3)

wherein
 (a) m is an integer from 0 to 10, preferably from 0 to 5, more preferably 0 or 1, more preferably 0;
 (b) $R^1$ and Y are as described hereinbefore; and
 (c) $R^2$ is hydrogen, lower alkyl or acyl derived from a carboxylic acid of a lower alkyl (9) an oxygen-containing moiety having the general structure:

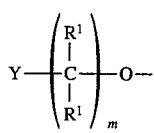

$$Y\left(\begin{array}{c} R^1 \\ | \\ \text{—C—} \\ | \\ R^1 \end{array}\right)_m \text{—O—} \qquad (4)$$

wherein
(a) m is an integer from 0 to 10, preferably from 0 to 5, more preferably 0 or 1, more preferably 0; and
(b) R1 and Y are as described hereinbefore

(10) sulfur-containing moiety having the general structure:

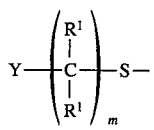

$$Y\left(\begin{array}{c} R^1 \\ | \\ \text{—C—} \\ | \\ R^1 \end{array}\right)_m \text{—S—} \qquad (5)$$

wherein
(a) m is an integer from 0 to 10, preferably from 0 to 5, more preferably 0 or 1, more preferably 0; and
(b) $R^1$ and Y are as described hereinbefore In Formula (1), "B" is hydrogen; halogen; unsubstituted or substituted lower alkyl; unsubstituted or substituted cycloalkyl having from 3 to 7 atoms in the ring; unsubstituted or substituted heterocycle having from 3 to 7 atoms in the ring; unsubstituted or substituted phenyl; hydroxy, or the ester thereof derived from a carboxylic acid of a lower alkyl group; thiol; unsubstituted amino, or the amide thereof derived from a carboxylic acid of a lower alkyl group; amino substituted with one lower alkyl group, or the amide thereof derived from a carboxylic acid of a lower alkyl group; amino substituted independently with two lower alkyl groups; or —$CO_2H$, the pharmaceutically-acceptable salt thereof, the ester thereof derived from an alcohol of a lower alkyl group, the unsubstituted amide thereof, or the amide thereof substituted with one or two lower alkyl groups.

To maintain chemical stability of these compounds, the A and B moieties preferably do not both have heteroatoms (nitrogen, oxygen or sulfur), or a heteroatom and a halogen, bonded to the phosphonate moiety (i.e., the carbon atom geminally substituted with the phosphorous atoms). Thus, when the A moiety has an oxygen, sulfur, nitrogen, or halogen atom bonded to the phosphorous-substituted methylene carbon, then B is selected from hydrogen; unsubstituted or substituted lower alkyl, cycloalkyl, heterocycle (where a carbon atom of the heterocycle is bonded to the geminal carbon atoms), or phenyl; —$CO_2H$, the pharmaceutically-acceptable salts thereof, the ester thereof derived from an alcohol of a lower alkyl group, the unsubstituted amide thereof, and the amide thereof substituted with one or two lower alkyl groups.

Preferably B is hydrogen, halogen, unsubstituted or substituted lower alkyl, unsubstituted or substituted phenyl, unsubstituted or substituted benzyl, hydroxy or the ester thereof derived from a carboxylic acid of a lower alkyl group, thiol, unsubstituted amino or the amide thereof derived from a carboxylic acid of a lower alkyl group, amino substituted with one lower alkyl group or the amide thereof derived from a carboxylic acid of a lower alkyl group, amino substituted independently with two lower alkyl groups, or —$CO_2H$ or the pharmaceutically-acceptable salts thereof and the ester thereof derived from an alcohol of a lower alkyl group and the unsubstituted amide thereof or the amide thereof substituted with one or two lower alkyl groups.

More preferably, B is hydrogen, chloro, methyl, ethyl, hydroxy, thiol, unsubstituted amino, (N-methyl)amino, (N,N-dimethyl)amino, —$CO_2H$ or the pharmaceutically-acceptable salts thereof, —$CO_2CH_3$, or —$CONH_2$. More preferably, B is hydrogen, methyl, chloro, amino, or hydroxy; more preferably hydrogen, or hydroxy, or amino, or thiol; more preferably hydroxy. Particularly preferred bone-active phosphonates include those wherein A is a moiety of groups (3) or (8) above, and B is hydroxy.

Particularly preferred bisphosphonates useful herein are of the formula:

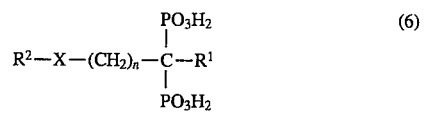

$$R^2\text{—X—}(CH_2)_n\text{—}\underset{\underset{PO_3H_2}{|}}{\overset{\overset{PO_3H_2}{|}}{C}}\text{—}R^1 \qquad (6)$$

wherein: n is an integer from 0 to 7 (preferably from 0 to 2, more preferably 1); $R^1$ is hydrogen, chloro, amino, or hydroxy (preferably hydrogen or hydroxy); X is —NH—, oxygen, or a single bond (preferably —NH— or single bond); $R^2$ is a 5- to 7-membered heterocycle having from 1 to 3 heteroatoms (preferably a 6-membered heterocycle having 1 or 2 nitrogen atoms), amino, amino substituted with one or two lower alkyl groups, or hydrogen; and their pharmaceutically-acceptable salts and esters.

The term "pharmaceutically-acceptable salts and esters", as used herein, means hydrolyzable esters and salts of the bone-active phosphonates which have the same general pharmacological properties as the acid form from which they are derived, and which are pharmaceutically acceptable. Pharmaceutically-acceptable salts include, for example, alkali metals (e.g., sodium and potassium), alkaline earth metals (e.g., calcium and magnesium), non-toxic heavy metals (e.g., stannous and indium), and ammonium and low molecular weight substituted ammonium (e.g., mono-, di- and triethanolamine) salts. Preferred compounds are the sodium, potassium, and ammonium salts. Pharmaceutically-acceptable esters include unsubstituted and substituted alkyl, aryl and phosphoryl esters. Nonlimiting examples of pharmaceutically-acceptable esters include, for example, isopropyl, tertiarybutyl, 2-chloroethyl, 2,2,2-trichloroethyl, 2,2,2-trifluoroethyl, p-toluenesulfonylethyl, glycyl, sarcosyl, benzyl, phenyl, 1,2-hexanoylglyceryl, p-nitrophenyl, 2,2 dimethyl-1,3-dioxolene-4-methyl, isopentenyl, o-carbomethoxyphenyl, piraloyloxymethylsalicylyl, diethylamidophosphoryl, pivaloyloxymethyl, acyloxymethyl, propionyloxymethyl, isobutyryloxymethyl, dodecyl, octadecyl, and isopropylo oxymethyl.

Specific examples and definitions for substituents useful in the compounds of Formulas (1) through (6) are described in European Patent Publication 298,553, Ebetino, published Jan. 11, 1989 (incorporated by reference herein). That application also describes phosphonoalkylphosphinates useful in the methods of this invention (wherein R is hydrogen or alkyl), and methods for making such compounds. Methods of making phosphonoalkylphosphinates are also described in European Patent Publication 298,555, Ebetino, published Jan. 11, 1989 (incorporated by reference herein).

Bisphosphonates useful in the methods of this invention (wherein R is hydroxy), and methods for making such compounds, are described in the following patent documents, all incorporated by reference herein: U.S. Pat. No. 3,553,314, Francis, issued Jan. 5, 1971; U.S. Pat. No. 3,683,080, Francis, issued Aug. 8, 1972; U.S. Pat. No. 3,846,420, Wollmann et al., issued Nov. 5, 1974; U.S. Pat. No. 3,899,496, Schindler et al., issued Aug. 12, 1975; U.S. Pat. No. 3,941,772, Ploger et al., issued Mar. 2, 1976; U.S. Pat. No. 3,957,160, Ploger et al., issued May 18, 1976; U.S. Pat. No. 3,962,432, Schmidt-Dunker, issued Jun. 8, 1976; U.S. Pat. No. 3,979,385, Wollmann et al., issued Sep. 7, 1976; U.S. Pat. No. 3,988,443, Ploger et al., issued Oct. 26, 1976; U.S. Pat. No. 4,054,598, Blum et al., issued Oct. 18, 1977; U.S. Pat. No. 4,113,861, Fleisch et al., issued Sep. 12, 1978; U.S. Pat. No. 4,117,090, Ploger, issued Sep. 26, 1978; U.S. Pat. No. 4,134,969, Schmidt-Dunker, issued Jan. 16, 1979; U.S. Pat. No. 4,267,108, Blum et al., issued May 12, 1981; U.S. Pat. No. 4,304,734, Jary et al., issued Dec. 8, 1981; U.S. Pat. No. 4,330,537, Francis, issued May 18, 1982; U.S. Pat. No. 4,407,761, Blum et al., issued Oct. 4, 1983; U.S. Pat. No. 4,469,686, Andrews, issued Sep. 4, 1984; U.S. Pat. No. 4,578,376, Rosini, issued Mar. 25, 1986; U.S. Pat. No. 4,608,368, Blum et al., issued Aug. 26, 1986; U.S. Pat. No. 4,621,077, Rosini et al., issued Nov. 4, 1986; U.S. Pat. No. 4,687,767, Bosies et al., issued Aug. 18, 1987; U.S. Pat. No. 4,687,768, Benedict et al., issued Oct. 18, 1987; U.S. Pat. No. 4,711,880, Stahl et al., issued Dec. 8, 1987; U.S. Pat. No. 4,719,203, Bosies et al., issued Jan. 12, 1988; U.S. Pat. No. 4,927,814, Gall et al., issued May 22, 1990; U.S. Pat. No. 4,990,503, Isomura et al., issued Feb. 5, 1991; German Offenlegungsschrift 2,104,476, Worms, published Aug. 17, 1972; German Offenlegungsschrift 2,343,147, Ploeger et al., published Apr. 3, 1975; German Offenlegungsschrift 2,360,798, Worms et al., published Jun. 26, 1975; German Offenlegungsschrift 2,513,966, Schmidt-Dunker, published Oct. 7, 1976; German Offenlegungsschrift 2,541,981, Eimers et al., published Mar. 24, 1977; German Offenlegungsschrift 3,334,211, Blum, published Apr. 4, 1985, Japanese Patent Publication 78/59,674, Suzuki et al., published May 29, 1978; Japanese Patent Publication 79/135,724, Suzuki et al., published Oct. 22, 1979; Japanese Patent Publication 80/98193, Suzuki et published Jul. 25, 1980; European Patent Publication 88,359, Blum et al., published Sep. 14, 1983; European Patent Publication 100,718, Breliere et al., published Feb. 15, 1984 ; European Patent Publication 186,405, Benedict et al., published Jul. 2, 1986; European Patent Publication 197,478, Bosies et al., published Oct. 15, 1986; European Patent Publication 230,068, Benedict et al., published Jul. 29, 1987; European Patent Publication 273,514, Ebetino et al., published Jul. 6, 1988; European Patent Publication 274,158, Ebetino et al., published Jul. 13, 1988; European Patent Publication 282,309, Sakamoto et al., published Sep. 14, 1988; European Patent Publication 282,320, Isomura et al., published Sep. 14, 1988; PCT Patent Publication 87/03598, Binderup et al., published Jun. 18, 1987; and PCT Patent Publication 88/00590, Gall et al., published Jan. 28, 1988.

Preferred bone-active phosphonates useful in the methods of this invention include: N-(2'-(3'-methyl)-pyridinyl)aminomethane phosphonomethylphosphinic acid; N-(2'-(5'-methyl)-pyridinyl)amino methane phosphonomethylphosphinic acid; N-(2'-(3'-methyl)-piperidinylidene)aminomethane phosphonomethylphosphinic acid; N-(2'-(5'-methyl)-piperidinylidene)aminomethane phosphonomethylphosphinic acid; 2-(2'-pyridinyl)ethane-1-phosphono-1-methylphosphinic acid; 2-(2'-piperidinyl)ethane-1-phosphono-1-methylphosphinic acid; 2-(p-aminophenyl)-1-hydroxy-ethane-1o-phosphono-1-methylphosphinic acid; 2-(m-aminophenyl)-1-hydroxy-ethane-1-phosphono-1-methylphosphinic acid; N-(1-(5-amino-2-methyl-1-oxo)-pentyl)aminomethane phosphonomet hylphosphinic acid; N-(2'-(3'-methyl)-piperidinylidene)aminomethane phosphonobutylphosphinic acid; S-(2'-pyridinyl)thiomethane phosphonomethylphosphinic acid; 2-(2-pyridyl)-1-hydroxyethane-1-phosphono-1-methyl phosphinic acid; 2-(3-pyridyl)-1-hydroxyethane-1-phosphono-1-methylphosphinic acid; 2-(N-imidazoyl)-1-hydroxyethane-1-phosphono-1-methylphosphinic acid; 3-(N-pentyl-N-methylamino)-1-hydroxypropane-1-phosphono-1-methylphosphinic acid; 4-amino-1-hydroxybutane-1-phosphono-1-methlphosphinic acid; 3-(N-pyrollidino)-1hydroxypropane-1-phosphono-1-methylphosphinic acid; N-cycloheptyl aminomethanephosphonomethylphosphinic acid; S-(p-chlorophenyl) thiomethanephosphonomethylphosphinic acid; (7-dihydro-1-pyrindine)methanephosphonomethylphosphinic acid; (7-dihydro-1-pyrindine)hydroxymethanephosphonomethylphosphinic acid; (6-dihydro-1-dihydro-2-pyrindine)hydroxymethanephosphonomethylphosphinic acid; 2-(6-pyrolopyrindine)-1-hydroxyethane-1-phosphono-1-methyl phosphinic acid; 1-hydroxyethane-1,1-bisphosphonic acid; 1-hydroxy pentane-1,1-bisphosphonic acid; methane bisphosphonic acid; dichloromethanebisphosphonic acid; hydroxymethanebisphosphonic acid; 1-aminoethane-1,1-bisphosphonic acid; 2-aminoethane-1,1-bisphosphonic acid; 3-aminopropane-1,1-bisphosphonic acid; 3-aminopropane-1-hydroxy-1,1-bisphosphonic acid; 3-(dimethylamino)-1-hydroxypropane-1,1-bisphosphonic acid; 3,3-dimethyl-3-amino-1-hydroxypropane-1,1-bisphosphonic acid; phenylaminomethane bisphosphonic acid; N,N-dimethylaminomethane bisphosphonic acid; N-(2-hydroxyethyl) aminomethane-6isphosphonic acid; 4-amino-1-hydroxybutane-1,1-bisphosphonic acid; 5-amino-1-hydroxypentane-1,1-bisphosphonic acid; 6-amino-1-hydroxyhexane-1,1-bisphosphonic acid; indan-2,2-bisphosphonic acid; hexahydroindan-2,2-bisphosphonic acid; 2-methylcyclobutane-1,1-bisphosphonic acid; 3-chlorocyclopentane-1,1-bisphosphonic acid; cyclohexane-1,1-bisphosphonic acid; 2-(2-pyridyl)-1-hydroxyethane-1,1-bisphosphonic acid; N-(2-(5-amino)-pyridyl)-aminomethane bisphosphonic acid; N-(2-(5-chloro)-pyridyl)-aminomethane bisphosphonic acid; N-(2-(3-picolyl))-aminomethane bisphosphonic acid; N-(2-(4-picolyl))-aminomethane bisphosphonic acid; N-(2-(5-picolyl))-aminothane bisphosphonic acid; N-(2-(6-picolyl))-aminomethane bisphosphonic acid; N-(2-(3,4-lutidine))-aminomethane bisphosphonic acid; N-(2-pyrimidyl)-aminomethane bisphosphonic acid; N-(2-pyridyl)-2-aminoethane-1,1-bisphosphonic acid; 2-(2-pyridyl)-ethane-1,1-bisphosphonic acid; 2-(3-pyridyl)-ethane-1,1-bisphosphonic acid; 2-(4-pyridyl)-ethane-1,1-bisphosphonic acid; 2-(2-(3-picolyl))-oxaethane-1,1-bisphosphonic acid; 2-(3-pyridyl)-1-hydroxyethane-1,1-bisphosphonic acid; 2-(3-pyridyl)-1-hydroxyethane-1,1-bisphosphonic acid; 2-(N-imidazoyl)-1-hydroxyethane-1,1-bisphosphonic acid; 3-(N-pentyl-N-methylamino)-1-hydroxypropane-1,1-bisphosphonic acid; 3-(N-pyrollidino)-1-hydroxypropane-1,1-bisphosphonic acid; N-cycloheptylaminomethane bisphosphonic acid; S-(p-chlorophenyl)thiomethanebisphosphonic acid; (7-dihydro-1 -pyrindine)methanebisphosphonic acid; (7-dihydro-1-pyrindine)hydroxymethanebisphosphonic acid; (6-dihydro-2-pyrindine)hydroxymethanebisphosphonic acid; 2-(6-pyrolopyridine)-1-hydroxyethane-1,1-bisphosphonic acid; and pharmaceutically-acceptable salts and esters thereof.

Particularly, preferred bone-active phosphonates useful in the methods of this invention include: 1-hydroxyethane-1,1-bisphosphonic acid; dichloromethane bisphosphonic acid; 3-amino-1-hydroxypropane-1,1-bisphosnic 6-amino-1-hydroxyhexane-1,1-bisphosphonic acid; 4-amino-1-hydroxybutane-1,1-bisphosphonic acid; 2-(3-pyridyl)-1-hydroxyethane-1,1-bisphosphonic acid; 2-(N-imidazoyl)-1-hydroxyethane-1,1-bisphosphonic acid; 3-N-pentyl-N-methylamino)-1-hydroxypropane-1,1-bisphosphonic acid; 3-(N-pyrollidino)-1-hydroxypropane-1,1-bisphosphonic acid; N-cycloheptylaminomethanebisphosphonic acid; S-(p- chlorophenyl) thiomethanebisphosphonic acid; (7-dihydro-1-pyrindine)methane bisphosphonic acid; (7-dihydro-1-pyrindine)hydroxymethane bisphosphonic acid; (6-dihydro-2-pyrindine)hydroxymethanebisphosphonic acid; 2-(6-pyrolopyridine)-1-hydroxyethane-1,1-bisphosphonic acid; and pharmaceutically-acceptable salts and esters thereof.

Parathyroid Hormone:

The methods of this invention also involve administration of parathyroid hormone. As referred to herein, "parathyroid hormone" refers to the naturally occurring human parathyroid hormone, synthetic analogs thereof, parathyroid hormone and parathyroid hormone fragments manufactured by recombinant DNA technology, and par athyroid hormone fragments and parathyroid hormone fragment analogs. Parathyroid hormone useful in the methods of this invention includes, for example hPTH (1-38), hPTH (1-34), hPTH (1-37). Detailed descriptions of the types of parathyroid hormones available and methods for manufacturing parathyroid hormone are disclosed in the following references, all incorporated by reference herein, U.S. Pat. No. 4,105,602, Colescott, et al., issued Aug. 8, 1978; U.S. Pat. No. 4,698,328, Neer, et al., issued Oct. 6, 1987; U.S. Pat. No. 4,833,125, Neer, et al., issued May 23, 1987; DE 32 43 358, Hesch, publication date May 24, 1984; and DE 39 35 738, Forssmann, et al., publication date May 8, 1991.

Methods of Treatment

This invention provides methods for increasing bone mass in a human or other animal subject afflicted with osteoporosis, comprising a thirty(30)-day treatment period, comprised of a parathyroid hormone administration regimen and a bisphosphonate administration regimen, wherein (a) said parathyroid hormone administration regimen comprises the administration to said subject of parathyroid hormone at a level of from about 4 IU/kg per day to about 15 IU/kg per day that said parathyroid hormone is administered, provided that said parathyroid hormone is administered at least one day every seven days of every said thirty(30)-day treatment period; and wherein (b) said bisphosphonate administration regimen comprises the administration to said subject of a bisphosphonate at a level of from about 0.0005 mgP/kg to about 1.0 mgP/kg per day that said bisphosphonate is administered, provided that said bisphosphonate is administered at least 1 day of every said thirty(30)-day treatment period.

Accordingly, the thirty(30)-day treatment period is comprised of a separate administration regimen for each active, i.e. one for the parathyroid hormone and one for the bisphosphonate. The parathyroid hormone must be given at least one day every seven days of every thirty(30)-day treatment period in order to maintain the physiological effect of the parathyroid hormone in the subject being treated. The parathyroid hormone may also be given every day of said thirty(30)-day treatment period, or every other day, or every third day, or every fourth day, or every fifth day, or every sixth day of said thirty(30)-day treatment period. The only limitation is that the parathyroid hormone must be given at a dose of 4–15 IU/kg per day on at least one day out of every seven days of said thirty(30)-day treatment period. As long as the parathyroid hormone is given at a dose of 4–15 IU/kg per day, it may be given at different doses within the 4–15 IU/kg per day range on different days, so long as it is given once every seven days of said thirty(30)-day treatment period. It may be desirable to administer one type of parathyroid hormone on some treatment days and another type on another treatment day.

In addition, a bisphosphonate must be given at least one day of every thirty(30)-day treatment period. However, a bisphosphonate may be given every day of said thirty(30)-day treatment period, or every other day of said thirty(30)-day treatment period, or every third day, or every fourth day, or every fifth day, or every sixth day of said thirty(30)-day treatment period. The only limitation is that the bisphosphonate must be given at a dose of 0.0005 mgP/kg–1.0 mgP/kg per day on at least one day of said thirty(30)-day treatment period. As long as the bisphosphonate is given at a dose of 0.0005 mgP/kg–1.0 mgP/kg per day, it may be given at a different dose within the 0.0005 mgP/kg–1.0 mgP/kg range on different days, so long as it is given on at least one day of said thirty(30)-day treatment period. It may be desirable to administer one type of bisphosphonate on some treatment days, and another type on another treatment day.

These treatment regimens are utilized sequentially, one after the other, until net skeletal mass is attained. Illustrative, but non-limiting, examples of the treatment regimens possible according to the methods of this invention are described herein: 1) parathyroid hormone is administered at a level of about 13 IU/kg per day for every day of said thirty(30)-day treatment period; on the seventh (7th) day of said thirty(30)-day treatment period a high potency bisphosphonate is administered at a level of about 0.001 mgP/kg per day for one (1) day, 2) a medium potency bisphosphonate is administered at a level of about 0.01 mgP/kg per day for five (5) days; on the sixth (6th) day parathyroid hormone is administered at a level of 5 IU/kg per day for fifteen (15) days; on the twenty-first (21st) day a medium potency bisphosphonate is administered for five (5) days, and on the twenty-sixth (26th) day parathyroid hormone is administered for five (5) days, 3) a medium potency bisphosphonate is administered at a level of about 0.002 mgP/kg per day for fourteen (14) days; on the fourth (4th) day parathyroid hormone is administered at a level of 5 IU/kg per day for twenty-six (26) days, 4) parathyroid hormone is administered for thirty (30) days at a level of about 4 IU/kg per day; on the fifteenth (15th) day a low potency bisphosphonate is administered at a level of about 0.2 mgP/kg per day for five (5) days, 5) parathyroid hormone is administered for thirty (30) days at a level of 8 IU/kg per day; on the tenth (10th), seventeenth (17th), and twenty-third (23rd) day a high potency bisphosphonate is administered at a level of 0.001 mgP/kg per day, 6) a low potency bisphosphonate is administered at a level of about 0.2 mgP/kg per day for fourteen (14) days; and on the seventh (7th) day parathyroid hormone is administered at a level of about 4 IU/kg per day for twenty-three (23) days, 7) a high potency bisphosphonate is administered at a level of about 0.01 mgP/kg per day for twenty (20 ) days; on the seventh (7th ) day parathyroid hormone is administered every other day at a level of about 10 IU/kg per day for twenty-three (23) days, 8) a medium potency bisphosphonate is administered every other day at a level of about 0.02 mgP/kg per day for seven (7) days; and on the third (3rd) day parathyroid hormone is administered at a level of about 10 IU/kg per day for fifteen (15) days; and on the eighteenth (18th) day bisphosphonate is administered every other day for twelve (12) days at a level of about 0.02 mgP/kg per day; and on the twenty-fifth (25th) day parathyroid hormone is administered at a level of 10 IU/kg per day for five (five) days, 9) parathyroid hormone is administered at a level of about 4 IU/kg per day for fifteen (15) days; on the twentieth (20th) and twenty-fifth (25th) day a high potency bisphosphonate is administered at a level of about 0.002 mgP/kg per day, and on the twenty-third (23rd) and twenty-seventh (27th) day parathyroid hormone is administered at a level of about 4 IU/kg per day.

The terms "low potency", "medium potency", and "high potency" are used to describe the bone antiresorptive capacity of the bisphosphonate. For example, low potency bisphosphonates have an LED of 1.0–0.5; medium potency bisphosphonates have an LED of 0.5–0.03, and high potency bisphosphonates have an LED of greater than 0.03–0.0001.

The potency of a particular bisphosphonate can be expressed in terms of its "LED" or "least effective dose", which is the minimum dose of bisphosphonate expressed in mg P/kg that is effective, by itself, to cause a significant inhibition of bone resorption. The specific LEDs of the bisphosphonates will vary depending upon their chemical composition, and their method of administration (i.e., oral or parenteral). The lower the LED, the more potent the bisphosphonate and, generally, it is desirable to administer the high potency bisphosphonate in lower doses and on a fewer number of days in said thirty(30)-day treatment period. Likewise, the higher the LED, the less potent the bisphosphonate and, generally, it is desirable to administer the low potency bisphosphonate in higher doses and on a greater number of days in said thirty(30)-day treatment period.

In particular, the LEDs for the bone-active phosphonates may be determined using any of several art-recognized in vivo models. One such model is the thyroparathyroidectomized ("TPTX") rat model. In this model, compounds are evaluated for in vivo bone resorption inhibition potency, by measuring their ability to inhibit the increase of serum calcium levels caused by administration of parathyroid hormone in rats whose parathyroid gland has been removed. This model is described in Russell et al., 6 *Calcified Tissue Research* 183 (1970); Muhlbauer et al., 5 *Mineral Electrolite Metabolism* 296 (1981); U.S. Pat. No. 4,761,406, Flora et al., issued Aug. 2, 1988; and European Patent Publication 298,553, Ebetino, published Jan. 11, 1989; all of which are incorporated by reference herein.

Another model is the "Schenk Model", which measures the effects of bone-active phosphonates on bone growth in young rats. This model is described in Schenk et al., 11 *Calcif. Tissue Res.* 196 (1973); Shinoda et al., 35 *Calcif. Tissue Int.* 87 (1983); U.S. Pat. No. 4,761,406, Flora et al., issued Aug. 2, 1988; and European Patent Publication 298, 553, Ebetino, published Jan. 11, 1989; all of which are incorporated by reference herein.

Another model is the "ovariectomized" or "OVX" rat model, which measures the ability of bone-active phosphonates to prevent loss of bone in female rates induced by ovariectomy. This model is described in Wronski et al., 125 *Endocrinology* 810 (1989), incorporated by reference herein.

The LEDs for parenteral dosing of preferred bone-active phosphonates useful herein are: 1.0 mg P/kg, for 1-hydroxyethane-1,1-bisphosphonic acid; 0.5 mg P/kg, for dichloromethane bisphosphonic acid; 0.03 mg P/kg, for 3-amino-1-hydroxypropane-1,1-bisphosphonic acid; 0.001 mg P/kg, for 4-amino-1-hydroxybutane-1,1-bisphosphonic acid; 0.1 mg P/kg, for 6-amino-1-hydroxyhexane-1,1-bisphosphonic acid; 0.01 mg P/kg, for N-(2pyridyl) aminomethane-1,1-bisphosphonic acid; 0.0003 mg P/kg, for 2-(3-pyridyl)-1-hydroxyethane-1,1-bisphosphonic acid; 0.0001 mg P/kg, for N-cycloheptyl-aminomethanebisphosphonic acid; 0.0001 mg P/kg, for 3-(N-pentyl-N-methylamino)-1-hydroxypropane-1,1-bisphosphonic acid; 0.01 mg P/kg, for 3-(dimethylamino)-1-hydroxypropane-1,1-bisphosphonic acid; 0.01 mg P/kg, for 3-(N-pyrollidino)-1-hydroxypropane-1,1-bisphosphonic acid; 0.03 mg P/kg, for N-cycloheptylaminomethanebisphosphonic acid; and 0.3 mg P/kg for S-(p-chlorophenyl)thiomethanebisphosphonic acid. (The LEDs for oral dosing would be higher, depending upon the systemic absorption of the phosphonate. Typically, absorption from oral administration is from about 1% to about 10%. Thus, oral LEDs are typically about ten- to one hundred-fold higher than the parenteral LEDs.)

As used herein, the term "mg P/kg" refers to the amount of compound, expressed as milligrams phosphorus in the compound, per kilogram weight of the subject to be treated. Because the bisphosphonates vary in molecular weight, expressing the amount administered in mg P/kg normalizes the comparison between bisphosphonates of varying potencies. In order to determine the mg P/kg administered to a patient according to the methods of this invention, the following conversion formula is used:

$$\text{mg/kg compound administered} = \frac{\text{mg } P}{\text{kg}} \times \frac{\text{molecular weight of the drug}}{\text{molecular weight of two phosphorus atoms}}$$

For example, 2-(3-pyridinyl)-1-hydroxyethane-1,1-bisphosphonate has a molecular weight of 350. Two phosphorus atoms have a molecular weight of 62. Thus, if a patient is dosed at 0.01 mg/kg of the compound, then about 0.002 mg P/kg was administered.

Parathyroid hormone is routinely dosed in International Units (IU).

The methods of this invention comprise treatment of osteoporosis at all stages of the disorder. Since osteoporosis is an ongoing process of bone loss, rather than a disorder having a discrete beginning- or end-point, "treatment", as referred to herein, consists of any method which stops, slows, or reverses the process of bone loss which occurs in osteoporosis.

Preferred methods of this invention comprise treatment of osteoporosis in subjects who have already lost skeletal mass (herein referred to as "established osteoporosis"). Such methods of this invention for the treatment of established osteoporosis preferably comprise administering the actives for a period of time sufficient to achieve an increase in the net skeletal mass of said subject. The increase in mass may be in cortical bone, trabecular bone, or both. Preferably, the net skeletal mass is increased by about 1% per year.

The specific period of time sufficient to achieve an increase in the net skeletal mass of the subject may depend on a variety of factors. Such factors include, for example, the specific actives employed, the amount of actives administered, the age and sex of the subject, the specific disorder to be treated, concomitant therapies employed (if any), the general physical health of the subject (including the presence of other disorders), the extent of bone loss in the individual, and the nutritional habits of the individual.

The therapeutic regimen utilizing the methods of this invention are preferably continued for at least about twelve months. Of course, a therapeutic regimen may be continued indefinitely, according to sound medical practice. Preferably the subject is treated until a net skeletal mass is obtained commensurate with reduced fracture risk as assessed by the patient's physician.

In the methods of this invention, "administering" refers to any method which, in sound medical practice, delivers the actives used in this invention to the subject to be treated in such a manner so as to be effective in the building of bone. The actives may be administered by any of a variety of known methods of administration, e.g., orally, dermatomucosally (for example, dermally, sublingually, intranasally, and rectally), parenterally (for example, by subcutaneous injection, intramuscular injection, intra-articular injection, intravenous injection), and by inhalation. Thus, specific modes of administration include, but are not limited to, for example, oral, transdermal, mucosal, sublingual, intramuscular, intravenous, intraperitoneal, subcutaneous administration, and topical application.

A preferred method for the treatment of osteoporosis includes an initial diagnostic step, to determine the presence of the disorder. Thus, a preferred method of this invention comprises the steps of performing a diagnostic on a human subject for the detection of osteoporosis and, upon obtaining a positive result from said diagnostic, administering the actives according to the methods of this invention. For such methods for treatment of postmenopausal female subjects prior to significant bone loss, said initial diagnostic step comprises performing a diagnostic for determining menopause. Such methods are well known in the art, and include determination of the bone mass and rate of bone remodeling. The rate of bone remodeling can be determined by measurement of biochemical markers See, Hui, et al., "The Contribution of Bone Loss to Postmenopausal Osteoporosis," 1 *Osteoporosis Int.* 30 (1990), incorporated by reference herein.

Suitable diagnostics for the detection of established osteoporosis are also well known in the art. Such methods include the measurement of the radiodensity of skeletal radiographs, quantitative computerized tomography, single energy photon absorptiometry, and dual-energy photon absorptiometry. Diagnostic techniques among those useful herein are described in W. A. Peck et al., Physician's Resource Manual on Osteoporosis (1987), published by the National Osteoporosis Foundation (incorporated by reference herein).

Dosage Forms:

The bone-active phosphonate and parathyroid hormone may be administered in any of a variety of pharmaceutically-acceptable compositions. Such compositions may comprise an active and a pharmaceutically-acceptable carrier. Pharmaceutically-acceptable carriers include solid or liquid filler diluents or encapsulating substances, and mixtures thereof, that are suitable for administration to a human or lower animal. The term "compatible", as used herein, means that the components of the pharmaceutical composition are capable of being commingled with the actives, and with each other, in a manner such that there is no interaction which would substantially reduce the pharmaceutical efficacy of the pharmaceutical composition under ordinary use situations. Pharmaceutically-acceptable carriers must, of course, be of sufficiently high purity and sufficiently low toxicity to render them suitable for administration to the human or lower animal being treated.

Some examples of the substances which can serve as pharmaceutical carriers are: sugars, such as lactose, glucose and sucrose; starches, such as corn starch and potato starch; cellulose and its derivatives, such as sodium carboxymethylcellulose, ethylcellulose, cellulose acetate; powdered tragacanth; malt; gelatin; talc; stearic acid; magnesium stearate; vegetable oils, such as peanut oil, cottonseed oil, sesame oil, olive oil, corn oil and oil of theobroma; polyols such as propylene glycol, glycerin, sorbitol, mannitol, and polyethylene glycol; agar; alginic acid; pyrogen-free water; isotonic saline; phosphate buffer solutions; wetting agents and lubricants such as sodium lauryl sulfate; coloring agents; flavoring agents; and preservatives. Other compatible pharmaceutical additives and actives may be included in the pharmaceutically-acceptable carrier for use in the compositions of the present invention.

The choice of a pharmaceutically-acceptable carrier to be used in conjunction with the active is determined by the way the active is to be administered. If the active is to be injected, the preferred pharmaceutical carrier is sterile water, physiological saline, or mixtures thereof. The pH of such parenteral composition is preferably adjusted to about 7.4. Suitable pharmaceutically-acceptable carriers for topical application include those known in the art for use in creams, gels, tapes, patches, and similar topical delivery means.

The pharmaceutically-acceptable carrier employed in conjunction with the actives is used at a concentration sufficient to provide a practical size to dosage relationship. The pharmaceutically-acceptable carriers, in total, may comprise from about 0.1% to about 99.9% by weight of the pharmaceutical compositions of the present invention, preferably from about 5% to about 80%, and most preferably from about 10% to about 50%.

A preferred method of administering bisphosphonates is orally, in a unit-dosage form (i.e., a dosage form containing an amount of active suitable for administration in one single dose, according to sound medical practice). Preferred unit dosage forms for bisphosphonate include tablets, capsules, suspensions, and solutions, comprising a safe and effective amount of active. Pharmaceutically-acceptable carriers suitable for the preparation of unit dosage forms for oral administration are well known in the art. Their selection will depend on secondary considerations like taste, cost, shelf stability, which are not critical for the purposes of the present invention, and can be made without difficulty by a person skilled in the art. Preferably, oral unit dosage forms of the bone-active phosphonate comprise from about 0.0005 mgP/kg oral per day to about 1.0 mgP/kg oral per day of the phosphonate.

A preferred method of administering parathyroid hormone is via subcutaneous injection in a unit dosage form. Preferred unit dosage forms for injectable parathyroid hormone include sterile solutions of water, physiological saline, or mixtures thereof. The pH of said solutions should be adjusted to about 7.4. Preferably, unit dosage forms of parathyroid hormone comprise from about 4 IU to about 15 IU per kg per day.

Kits:

This invention also provides kits for conveniently and effectively implementing the methods of this invention. Such kits comprise one or more unit doses of bone-active phosphonate, one or more unit doses of parathyroid hormone, and a means for facilitating compliance with methods of this invention. Such kits provide a convenient and effective means for assuring that the subject to be treated takes the appropriate active in the correct dosage in the correct manner. The compliance means of such kits includes any means which facilitates administering the actives according to a method of this invention. Such compliance means includes instructions, packaging, and dispensing means, and combinations thereof. Examples of packaging and dispensing means are well known in the art, including those described in U.S. Pat. No. 4,761,406, Flora et al., issued Aug. 2, 1988; and U.S. Pat. No. 4,812,311, Uchtman, issued Mar. 14, 1989 and U.S. Pat. No. 4,833,125, Neer et al., issued May 23, 1989, all incorporated by reference herein.

The following non-limiting examples illustrate the compositions, processes and uses of the present invention.

EXAMPLE 1

A human Caucasian female patient weighing approximately 60 kg and diagnosed with postmenopausal osteoporosis is treated by a method of this invention. Specifically for one year:

1) parathyroid hormone (human synthetic fragment 1-34, or h PTH 1-34 is self-administered subcutaneously at a dose of 13 IU/kg via insulin syringe to the anterior thigh for five days out of every week, and 2) the bisphosphonate, 2-(3-pyridyl)-1-hydroxyethane-1,1-bisphosphonic acid, is taken orally as a tablet containing 0.002 mgP/kg per day.

A biopsy of iliac crest bone is taken at one year and reveals an increase in mean wall thickness of the remodeling units (BMU) compared to her baseline biopsy. The activation frequency and depth of resoration cavities on cancellous, cortical and endocortical surfaces are not significantly increased above the values observed at baseline.

EXAMPLE 2

A human African-American male (with a history of atraumatic fractures) weighing approximately 68 kg is treated for idiopathic osteoporosis by a method of this invention. Specifically each day for two years the patient self-administers an injection of parathyroid hormone (h PTH 1-38) subcutaneously at a dose of 8 IU/kg. In addition, once a week is taken the bisphosphonate, 4-amino-1-hydroxybutane-1,1-bisphosphonic acid, orally as a tablet containing 0.03 mgP/kg per day. The therapeutic response of cancellous bone is monitored by quantitative computed tomography of the spine; at the end of two years the patient demonstrated an increase of 14.5 mg/cc spinal bone mineral from his baseline value. The response of therapy to cortical bone is measured by single photon absorptiometry of the radius which shows no loss of bone mineral content (and in fact a slight gain) from the baseline measurement. No further atraumatic fractures were observed.

EXAMPLE 3

A human Oriental female subject with chronic asthma weighing about 60 kg is diagnosed with glucocorticoid-induced osteoporosis. The subject i s then treated by a method of this invention. Specifically the subject administers h PTH 1-34 as a daily nasal spray delivering 5 IU/kg. In addition, the subject applies a transdermal patch on a weekly basis which delivers a daily systemic dose of 0.005 mgP/kg per day of the bisphosphonate, 3-amino-1-hydroxypropane-1,1-bisphosphonic acid. After one month on therapy, a blood sample is obtained and analyzed for the bone specific marker, osteocalcin, and bone-derived and total alkaline phosphatase. Osteocalcin values are increased by 57% and both bone and total alkaline phosphatase are slightly elevated compared to pretreatment values. These findings are consistent with increased osteoblast function without greatly accelerated bone turnover.

EXAMPLE 4

A human Caucasian male approximately 65 kg was treated with a method of this invention, namely, treatment with parathyroid hormone followed closely with treatment with the bisphosphonate, 1-hydroxyethane-1,1-bisphosphonate. Specifically, parathyroid hormone hPTH 1-34 was self-administered by injection for 3 months at 10 IU/kg. A bone density scan by dual photon absorptiometry revealed an increase in bone mass. To maintain this gain, the parathyroid hormone administration was stopped and he was prescribed a course of the bisphosphonate, 1-hydroxyethane-1, 1-bisphosphonate, to begin the next week and continue for 3 months as a tablet containing 0.90 mgP/kg per day taken orally for one day each week. A bone densitometry assessment at the end of the 1-hydroxyethane-1,1-bisphosphonate therapy showed a maintenance of bone mass. The subject would be put back on parathyroid hormone if at the end of the next 3-month period significant bone loss had occurred.

What is claimed is:

1. A method of increasing bone mass in a human or other animal subject afflicted with osteoporosis, consisting essentially of a thirty(30)-day treatment period, consisting essentially of a parathyroid hormone administration regimen and bisphosphonate administration regimen, wherein (a) said parathyroid hormone administration regimen consists essentially of the administration to said subject of parathyroid hormone at a level of from about 4 IU/kg per day to about 15 IU/kg per day that said parathyroid hormone is administered, provided that said parathyroid hormone is administered at least one day every seven days of every said thirty(30)-day treatment period; and wherein (b) said bisphosphonate administration regimen consists essentially of the administration to said subject of a bisphosphonate at a level of from about 0.0005 mgP/kg to about 1.0 mgP/kg per day that said bisphosphonate is administered, provided that said bisphosphonate is administered at least 1 day of every said thirty(30)-day treatment period.

2. A method of increasing bone mass in a human or other mammal subject afflicted with osteoporosis, according to claim 1, before a significant loss of net skeletal mass has occurred in said subject.

3. A method of increasing bone mass in a human or other mammal subject afflicted with osteoporosis, according to claim 1, wherein said bone-active phosphonate is a bisphosphonic acid, or a pharmaceutically-acceptable salt or ester thereof.

4. A method of increasing bone mass in a human or other mammal subject afflicted with osteoporosis, according to claim 1, wherein said bisphosphonic acid is of the formula:

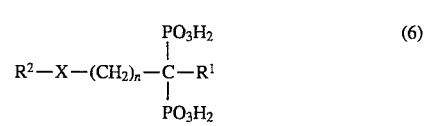

wherein: n is an integer from 0 to 7; $R^1$ is hydrogen, chloro, amino, or hydroxy; X is —NH—, oxygen, or a single bond; $R^2$ is a 5- to 7-membered herocycle having from 1 to 3 heteroatoms, amino, amino substituted with one or two lower alkyl groups, or hydrogen; and their pharmaceutically-acceptable salts and esters.

5. A method of increasing bone mass in a human or other mammal subject afflicted with osteoporosis, according to claim 1, wherein said bisphosphonic acid is selected from the group consisting of: 1-hydroxyethane-1,1-bisphosphonic acid; dichoromethane bisphosphonic acid; 3-amino-1-hydroxypropane-1,1-bisphosphonic acid; 6-amino-1-hydroxyhexane-1,1-bisphosphonic acid; 4-amino-1-hydroxybutane-1,1-bisphosphonic acid; 2-(3-pyridyl)-1-hydroxyethane-1,1-bisphosphonic acid; 2-(N-imidazoyl)-1-hydroxyethane-1,1-bisphosphonic acid; 3-(N-pentyl-N-methlamino)-1-hydroxyethane-1,1-bisphosphonic acid; 3-(N-pyrollidino)-1-hydroxypropane-1,1-bisphosphonic acid; N-cycloheptylaminomethanebisphosphonic acid; S-(p-chlorophenyl)thiomethanebisphosphonic acid; (7-dihydro-1-pyridine)methanebisphosphonic acid; (7-dihydro-1-pyridine)hydroxymethanebisphosphonic acid; (6-dihydro-2-pyridine)hydroxymethanebisphosphonic acid; 2-(6-pyrolopyridine)-1-hydroxyethane-1,1-bisphosphonic acid; 2-(2-pyridyl)-1-hydroxy-ethane-1,1-bisphosphonic acid; and pharmaceutically-acceptable salts and esters thereof.

6. A method of increasing bone mass in a human or other mammal subject afflicted with osteoporosis, according to claim 5, wherein said bisphosphonic acid is 1-hydroxyethane-1,1-bisphosphonic acid, or a pharmaceutically acceptable salt or ester thereof.

7. A method of increasing bone mass in a human or other mammal subject afflicted with osteoporosis, according to claim 5, wherein said bisphosphonic acid is 2-(3-pyridyl)-1-hudroxethane-1,1-bisphosphonic acid, or a pharmaceutically acceptable salt or ester thereof.

8. A method of increasing bone mass in a human or other mammal subject afflicted with osteoporosis, according to claim 1, wherein said bone-active phosphonate is a phosphonoalkylphosphinate, or a pharmaceutically-acceptable salt or ester thereof.

9. A method of increasing bone mass in a human or other mammal subject afflicted with osteoporosis, according to claim 8, wherein said phosphonoalkylphosphinate is selected from the group consisting of: N-(2'-(3'-methyl)-pyridinyl)aminomethane phosphonomethylphosphinic acid; N-(2'-(5'-methyl)-pyridinyl)aminomethane phosphonomethylphosphinic acid; N-(2'-(3'-methyl)-piperidinylidene)aminomethane phosphonomethylphosphinic acid; N-(2'-(5'-methyl)-piperidinylidene)aminomethane phosphonomethyl phosphinic acid; 2-(2'-pyridinyl)ethane-1-phosphono-1-methylphosphinic acid; 2-(2'-piperidinyl)ethane-1-phosphono-1-methylphosphinic acid; 2-(p-aminophenyl)-1-hydroxyethane-1-phosphono-1-methylphosphinic acid; 2-(m-aminophenyl)-1-hydroxy-ethane-1-phosphono-1-methylphosphinic acid; N-(1-(5-amino-2-methyl-1-oxo)-pentyl)aminomethane phosphonomethylphosphinic acid; N-(2'-(3'-methyl)-piperidinylidene)aminomethane phosphonobutylphosphinic acid; S-(2'-pyridinyl)thiomethane phosphonomethylphosphinic acid; and 2-(2-pyridyl)-1-hydroxyethane-1-phosphono-1-methylphosphinic acid; 2-(3-pyridyl)-1-hydroxy ethane-1-phosphono-1-methylphosphinic acid; 2-(N-imidazoyl)-1-hydroxy ethane-1-phosphono-1-methylphosphinic acid; 3-(N-pentyl-N-methylamino)-1-hydroxpropane-1-phosphono-1-methyl phosphinic acid; 4-amino-1-hydroxybutane-1-phosphono-1-methylphosphinic acid; 3-(N-pyrollidino)-1-hydroxypropane-1-phosphono-1-methyl phosphinic acid; N-cycloheptylaminomethanephosphonomethylphosphinic acid; S-(p-chlorophenyl)thiomethanephosphonomethylphosphinic acid; (7-dihydro-1-pyridine)methanephosphonomethylphosphinic acid; (7-dihydro-1-pyridine)hydroxymethanephosphonomethyl phosphinic acid; (6-dihydro-2-pyridine)hydroxymethanephosphonomethylphosphinic acid; 2-(6-pyrolopyridine)-1-hydroxyethane-1-phosphono-1-methylphosphinic acid; and pharmaceutically-acceptable salts and esters thereof.

10. A method of increasing bone mass in a human or other mammal subject afflicted with osteoporosis, according to claim 1, wherein said parathyroid hormone is selected from the group consisting of h PTH (1-38), h PTH (1-34) and h PTH (1-37).

11. A method of increasing bone mass in a human or other mammal subject afflicted with osteoporosis, according to claim 1, wherein said parathyroid hormone is administered every day of said thirty(30)-day treatment period.

12. A method of increasing bone mass in a human or other mammal subject afflicted with osteoporosis, according to claim 1, wherein said parathyroid hormone is administered every other day of said thirty(30)-day treatment period.

13. A method of increasing bone mass in a human or other mammal subject afflicted with osteoporosis, according to claim 1, wherein said parathyroid hormone is administered every third day of said thirty(30)-day treatment period.

14. A method of increasing bone mass in a human or other mammal subject afflicted with osteoporosis, according to claim 1, wherein said bisphosphonate is administered every other day of said thirty(30)-day treatment period.

15. A method of increasing bone mass in a human or other mammal subject afflicted with osteoporosis, according to claim 1, wherein said bisphosphonate is administered every third day of said thirty(30)-day treatment period.

16. A method of increasing bone mass in a human or other mammal subject afflicted with osteoporosis, according to claim 1, wherein said bisphosphonate is administered every day of said thirty(30)-day treatment period.

17. A method of increasing bone mass in a human or other mammal subject afflicted with osteoporosis, consisting essentially of one or more thirty(30)-day treatment periods, comprised of a parathyroid hormone administration regimen, wherein said parathyroid hormone is a species of parathyroid hormone having 1–38 amino acid units, and bisphosphonate administration regimen, wherein, said bisphosphonate is 2-(3-pyridyl)-1-hydroxyethane-1,1-bisphosphonate, wherein, (a) said parathyroid hormone administration regimen comprises the administration to said subject of said parathyroid hormone at a level of from about 4 IU/kg per day to about 15 IU/kg per day that said parathyroid hormone is administered, provided that said parathyroid hormone is administered at least one day every seven days of every said thirty(30)-day treatment period; and wherein (b) said bisphosphonate administration regimen comprises the administration to said subject of said bisphosphonate at a level of from about 0.0005 mgP/kg to about 1.0 mgP/kg per day that said bisphosphonate is administered, provided that said bisphosphonate is administered at least 1 day of every said thirty(30)-day treatment period.

18. A method of increasing bone mass in a human or other mammal subject afflicted with osteoporosis, according to claim 17, before a significant loss of net skeletal mass has occurred in said subject.

19. A method of increasing bone mass in a human or other mammal subject afflicted with osteoporosis, according to claim 17, wherein said parathyroid hormone is administered every day of said thirty(30)-day treatment period.

20. A method of increasing bone mass in a human or other mammal subject afflicted with osteoporosis, according to claim 17, wherein said parathyroid hormone is administered every other day of said thirty(30)-day treatment period.

21. A method of increasing bone mass in a human or other mammal subject afflicted with osteoporosis, according to claim 17, wherein said parathyroid hormone is administered every third day of said thirty(30)-day treatment period.

22. A method of increasing bone mass in a human or other mammal subject afflicted with osteoporosis, according to claim 17, wherein said bisphosphonate is administered every other day of said thirty (30)-day treatment period.

23. A method of increasing bone mass in a human or other mammal subject afflicted with osteoporosis, according to claim 17, wherein said bisphosphonate is administered every third day of said thirty(30)-day treatment period.

24. A method of increasing bone mass in a human or other mammal subject afflicted with osteoporosis, according to claim 17, wherein said bisphosphonate is administered every day of said thirty(30)-day treatment period.

* * * * *